United States Patent
Martyn et al.

(10) Patent No.: US 9,119,897 B2
(45) Date of Patent: *Sep. 1, 2015

(54) DRY POWDER FIBRIN SEALANT

(75) Inventors: Glen Patrick Martyn, Leicestershire (GB); Jacob Koopman, Leiden (NL)

(73) Assignee: PROFIBRIX B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 13/322,754

(22) PCT Filed: May 28, 2010

(86) PCT No.: PCT/EP2010/057477

§ 371 (c)(1),
(2), (4) Date: Nov. 28, 2011

(87) PCT Pub. No.: WO2010/136588

PCT Pub. Date: Dec. 2, 2010

(65) Prior Publication Data

US 2012/0070477 A1    Mar. 22, 2012

(30) Foreign Application Priority Data

May 28, 2009  (GB) .................................. 0909137.2
May 28, 2009  (GB) .................................. 0909138.0

(51) Int. Cl.
A61L 24/10    (2006.01)
A61K 9/00     (2006.01)
A61K 9/14     (2006.01)
A61K 9/16     (2006.01)
A61K 47/26    (2006.01)

(52) U.S. Cl.
CPC ............. *A61L 24/106* (2013.01); *A61K 9/0024* (2013.01); *A61K 9/143* (2013.01); *A61K 9/146* (2013.01); *A61K 9/1623* (2013.01); *A61K 47/26* (2013.01)

(58) Field of Classification Search
None
See application file for complete search history.

(56) References Cited

U.S. PATENT DOCUMENTS

| 4,427,651 | A | * | 1/1984 | Stroetmann ................... 424/46 |
| 5,702,715 | A | * | 12/1997 | Nikolaychik et al. ........ 424/402 |
| 6,056,970 | A | * | 5/2000 | Greenawalt et al. .......... 424/426 |
| 6,113,948 | A | * | 9/2000 | Heath et al. .................. 424/499 |
| 6,632,457 | B1 |  | 10/2003 | Sawhney |
| 7,189,410 | B1 | * | 3/2007 | Drohan et al. ................. 424/447 |
| 2002/0001584 | A1 |  | 1/2002 | Metzner et al. |
| 2002/0037323 | A1 |  | 3/2002 | Prasch et al. |
| 2003/0181917 | A1 |  | 9/2003 | Gertner |
| 2004/0018228 | A1 | * | 1/2004 | Fischell et al. ................ 424/450 |
| 2004/0089606 | A1 | * | 5/2004 | Kirkland et al. .............. 210/656 |
| 2005/0123588 | A1 |  | 6/2005 | Zhu et al. |
| 2006/0034935 | A1 | * | 2/2006 | Pronovost et al. ............ 424/489 |
| 2006/0104970 | A1 | * | 5/2006 | Margel et al. ............... 424/94.64 |
| 2006/0110381 | A1 | * | 5/2006 | Pendharkar et al. ........ 424/94.64 |
| 2006/0127488 | A1 | * | 6/2006 | Pendharkar et al. .......... 424/489 |
| 2006/0155235 | A1 | * | 7/2006 | Sawyer .......................... 602/48 |
| 2006/0204490 | A1 | * | 9/2006 | Pendharkar et al. ........ 424/94.64 |
| 2007/0275028 | A1 | * | 11/2007 | Barry et al. ................... 424/422 |
| 2007/0276505 | A1 | * | 11/2007 | Barry et al. ................ 623/23.62 |
| 2008/0033331 | A1 |  | 2/2008 | MacPhee et al. |
| 2008/0033333 | A1 | * | 2/2008 | MacPhee et al. ............... 602/50 |
| 2008/0044852 | A1 | * | 2/2008 | Kanayinkal et al. .......... 435/68.1 |
| 2008/0241072 | A1 | * | 10/2008 | Barry et al. .................. 424/9.36 |
| 2009/0148502 | A1 | * | 6/2009 | Pronovost ..................... 424/447 |
| 2010/0047352 | A1 | * | 2/2010 | Pronovost et al. ............. 424/489 |
| 2010/0284998 | A1 |  | 11/2010 | Smith et al. |
| 2012/0064165 | A1 | * | 3/2012 | Koopman ..................... 424/489 |

FOREIGN PATENT DOCUMENTS

| CN | 1364889 A | 8/2002 |
| CN | 1454667 A | 11/2003 |
| CN | 1617735 A | 5/2005 |
| EP | 1157706 A2 | 11/2001 |
| EP | 1905443 A1 | 4/2008 |
| JP | 3258723 A | 11/1991 |
| WO | 9744015 A1 | 11/1997 |
| WO | 0024436 A1 | 5/2000 |
| WO | 03047530 A2 | 6/2003 |
| WO | 2006012541 A2 | 2/2006 |
| WO | 2009046194 A2 | 4/2009 |
| WO | 2010002435 A2 | 1/2010 |
| WO | 2010136589 A1 | 12/2010 |

OTHER PUBLICATIONS

Tissue-tissue adhesion-preventing materials contg. chitin(s)—prevent post-operating adhesion of wounds, and have high bio-absorbability, XP002249992.
Notification Concerning Transmittal and International Preliminary Report on Patentability dated Dec. 8, 2011 from corresponding International Application No. PCT/EP2010/057477 filed May 28, 2010.
Kilburn et al., Organization and mobility of water in amorphous and crystalline trehalose, Nature Publishing Group, 632-635, Aug. 2006.
Cannon et al., Rate of Epithelial Regeneration, Annals of Surgery, Jan. 1943, pp. 85-92.
Klemm, Enhanced Healing of Skin Wounds in Dogs with Systemically and Locally Administered Drugs, Specialia, 1967, pp. 55-57.
Maggos, C.; Title: "ProFibrix: Hemostatic sprinkles"; BioCentury, Mar. 26, 2007; p. A15.
Cesaro et al.; Title: Water interplay in trehalose polymorphism; Food Chemistry, vol. 106, pp. 1318-1328; published 2008.
Yi Xiaodong et al., Experimental study on long-term effect of employing Fibrin Sealant to prevent post-surgical epidurar scar adhesions, Clinical Surgery, Feb. 2005, vol. 13, Issue 2, pp. 101-102.

* cited by examiner

*Primary Examiner* — Robert A Wax
*Assistant Examiner* — Olga V Tcherkasskaya
(74) *Attorney, Agent, or Firm* — Young Basile

(57) ABSTRACT

A fibrin sealant comprises a mixture of first microparticles that comprise fibrinogen, second microparticles that comprise thrombin, and additive material. The additive material may be particulate, and may be, for instance, a biocompatible, water-absorbent, material, a biocompatible, water-swellable material, a biocompatible, water-insoluble material, a polysaccharide or silica.

19 Claims, 6 Drawing Sheets

T=0

T=20 min

T=45 min

T=76 min

T=106 min

T=175 min

T=238 min

T=48 hours

DRY POWDER FIBRIN SEALANT

TECHNICAL FIELD

This invention relates to a dry powder fibrin sealant.

BACKGROUND

WO97/44015 describes a dry powder fibrin sealant based on micro-particles of fibrinogen and thrombin. Improved sealants that overcome the disadvantages of that described in WO97/44015 are desired.

SUMMARY

In a first aspect of the invention, there is provided a novel fibrin sealant composition of the general type described in WO97/44105. Further optimized formulations of these microparticle compositions are described in co-pending application U.S. Ser. No. 12/636,718, herein incorporated by reference. In the Example of this US application, the components are prepared by spray-drying, fibrinogen with trehalose and thrombin with trehalose. Each product has a predominant particle size of up to 50 µm diameter. The fibrin sealant, a blend of these components, has been demonstrated to be an easy-to-use, stable and efficacious topical haemostat. The product can be used immediately, without reconstitution. On contact with aqueous fluid such as blood, the exposed active thrombin converts the exposed fibrinogen into insoluble fibrin polymers.

In a second aspect of the invention, there is provided a fibrin sealant composition, comprising a mixture of first microparticles that comprise fibrinogen, second microparticles that comprise thrombin, and further comprising additive material.

In a third aspect of the invention, there is provided a fibrin sealant composition, comprising a mixture of first microparticles that comprise fibrinogen and a stabilizing excipient, second microparticles that comprise thrombin and a stabilizing excipient, and further comprising additive material. A particularly preferred stabilizing excipient is trehalose.

In a fourth aspect of the invention, there is provided a fibrin sealant composition, comprising a mixture of first microparticles that comprise fibrinogen, second microparticles that comprise thrombin, and further comprising additive material, wherein the additive material comprises porous and/or soluble material.

In a fifth aspect of the invention, there is provided a fibrin sealant composition, comprising a mixture of first microparticles that comprise fibrinogen, second microparticles that comprise thrombin, and further comprising additive material, wherein the additive material comprises hollow and/or soluble material.

In a sixth aspect of the invention, there is provided a fibrin sealant composition, comprising a mixture of first microparticles that comprise fibrinogen, second microparticles that comprise thrombin, and further comprising additive material, wherein the additive material comprises a biocompatible, water-absorbent material.

In a seventh aspect of the invention there is provided a fibrin sealant composition, comprising a mixture of first microparticles that comprise fibrinogen, second microparticles that comprise thrombin, and further comprising additive material, wherein the additive material comprises a biocompatible, water-swellable material.

In an eighth aspect of the invention there is provided a fibrin sealant composition, comprising a mixture of first microparticles that comprise fibrinogen, second microparticles that comprise thrombin, and further comprising additive material, wherein the additive material is in the form of nanoparticles, nanofibres, fibres, particles, granules, powder, beads, microbeads, microspheres, microcapsules or microparticles.

In a ninth aspect of the invention there is provided a fibrin sealant composition, comprising a mixture of first microparticles that comprise fibrinogen, second microparticles that comprise thrombin, and further comprising additive material, wherein the additive material comprises a polysaccharide.

In a tenth aspect of the invention there is provided a fibrin sealant composition, comprising a mixture of first microparticles that comprise fibrinogen, second microparticles that comprise thrombin, and further comprising additive material, wherein the additive material comprises silica.

In an eleventh aspect, the invention provides a free-flowing powder comprising a composition according to the invention.

In a twelfth aspect, the invention provides a container comprising a composition according to the invention.

In a thirteenth aspect, the invention provides a kit comprising a composition according to the invention, or a container according to the invention, optionally with a dispensing device.

In a fourteenth aspect, there is provided a method of treating bleeding comprising the step of administering an effective amount of the fibrin sealant composition of the invention.

In a fifteenth aspect, the invention provides the use of the composition of the invention in the manufacture of a medicament for the prevention, treatment and/or alleviation of a condition, such as wound therapy and surgical repair.

The additive material can act as a carrier or diluent, may enhance powder flow and wettability and may also have the effect of increasing absorbance of fluid of the bleeding wound, thereby decreasing the local tissue fluid and hence increasing the relative concentration of clotting factors in the wound. The invention thus provides the use of any of the additives herein described to achieve any of these objectives. By this, the effectiveness of the fibrin sealant is increased. The invention also provides a fibrin sealant product that has efficacy at low fibrinogen levels.

BRIEF DESCRIPTION OF THE DRAWINGS

The various features, advantages and other uses of the present apparatus will become more apparent by referring to the following detailed description and drawing in which.

DETAILED DESCRIPTION

Figure 1A:
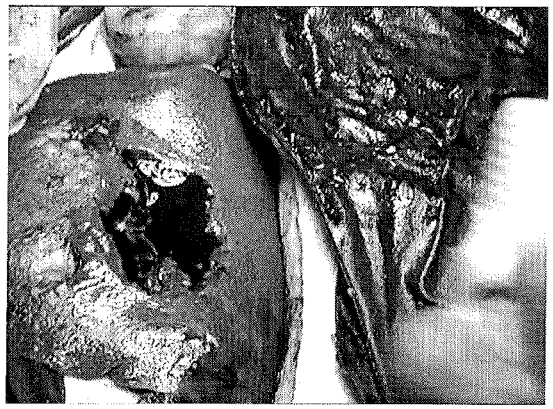
FIG. 1 shows photographs of a liver scallop injury model illustrating the utility of the present invention. The first frame (a) shows the injury that is made, the second frame (b) shows the Inventive Powder of Example 1 being applied, and the last frame (c) shows a Vicryl sheet covering the powder after 30 seconds of pressure with gauze.

Respective fibrinogen-containing and thrombin-containing soluble microparticles can be formulated and blended together, in stable, dry form. This formulation can be subsequently activated, as desired, to give a fibrin sealant that is useful in wound therapy and surgical repair.

The composition of the invention can meet the primary objectives of achieving good flow properties, enhanced wettability and enhanced, effective delivery to the active site, and dissolution only at the site, not in the delivery system.

The fibrinogen and the thrombin may be isolated from blood from human donors or be made by recombinant DNA technology in cultured cells or transgenic animals or plants.

The fibrinogen or thrombin may be full-length or any active fragment thereof. The content of fibrinogen in the microparticles containing it may be about 0.1 to 50% w/w, preferably about 0.5 to 20% w/w, as well as 5 to 10% w/w, or about 6.5% w/w. The content of thrombin in the microparticles containing it may be about 10 to 20,000 IU/g, preferably about 25 to 1000 IU/g, or 100 to 500 IU/g, or about 270 IU/g.

The active-containing microparticles and/or additive material may be solid or hollow, such as in the case of microcapsules. Microparticles comprising fibrinogen or thrombin may be prepared by methods known in the art, for example as described in WO 92/18164, WO 96/09814, WO 96/18388 or WO 97/44015. These spray-drying and associated particle manipulation processes enable the production of soluble protein microcapsules with defined size distribution, for example of up to 50 µm in diameter. For example, as described in those documents, the microparticles may be produced reproducibly, e.g. with 90% or more (by volume) up to 30 µm, e.g. 10 to 20 µm, in size. Readily-flowing agglomerates of these particles may be made in situ by adjusting the air flow configuration in the spray-dryer to counter-current, or arranging multiple atomisers into a "forced primary agglomeration" set-up, as would be appreciated by persons skilled in the art. Such agglomerates may be 50 to 1000 µm or 100 to 500 µm, or 125 to 250 µm in diameter. Respective fibrinogen-containing and thrombin-containing soluble microparticles can be formulated and blended together within a spray-drying apparatus by the use of a multi-nozzle atomizer, as described in WO03/037303.

Although the preferred method of preparation of the dry powder formulation includes spray drying, other drying techniques may also be used to prepare the dry powder formulation. Suitable methods are known in the art and include fluidized bed drying and freeze-drying, with subsequent micronisation, or spray-freeze drying. Microparticles may be sterilised, if necessary or desired, using techniques known in the art.

Microparticles of the invention are preferably prepared by spray-drying. Typically, a 2-fluid nozzle is used which utilises compressed air during the atomisation process; this results in the production of hollow microparticles. The maximum particle size of microparticles (X50, as measured by Sympatec) that can be manufactured using this atomisation system on the Niro Mobile Minor spray dryer is ~30 µm. Preferred X50 values for the micoparticles of the invention are between 5 and 50 µm, most preferably between 10 and 20 µm.

The solid or hollow fibrinogen-containing microparticles are then blended with the solid or hollow thrombin-containing microparticles and the additive material as described herein, in any sequence which produces a homogenous blend. Such blending can be carried out using low shear or high-shear blending, or any other technique known to persons skilled in the art.

The first or second microparticles of the invention may be prepared by spray-drying a solution of the active component, i.e. fibrinogen or thrombin, with a saccharide alone. An alternative procedure comprises co-spray-drying, in which fibrinogen or thrombin and another wall-forming material are formulated and spray-dried, to give microparticles in which the active component is incorporated into the particle.

The fibrinogen or thrombin may be full-length or any active fragment thereof. Fragments are known; see Coller et al, J. Clin. Invest. 89:546-555 (1992). Fibrinogen raw material may be a frozen solution, although, lyophilised powder which requires reconstitution prior to spray-drying may be used.

Suitable other proteins may be naturally occurring or be made by recombinant DNA technology in cultured cells or transgenic animals or plants. The fibrinogen or thrombin may be full-length or any active fragment thereof. They may act as "wall-forming materials", as described in WO92/18164, where various examples are given. A preferred material is HSA (human serum albumin). For example, fibrinogen is spray-dried alone or in the presence of varying amounts of excipients such as HSA (e.g. fibrinogen: HSA ratios of 1:1, 1:3, 3:1) and trehalose. Other suitable substitutes for HSA include surfactants, such as Tween 20, Tween 80, Poloxamer 407 or Poloxamer 188.

Calcium ions, e.g. as calcium chloride, may be incorporated in the thrombin feedstock. Alternatively, calcium chloride may be added to the microparticles after processing.

In preferred embodiments of the invention, the additive material is present in the form of discrete particles that are separate from the microparticles comprising fibrinogen and thrombin. Thus, the additive material may be in the form of nanoparticles, nanofibres, fibres, particles, granules, powder, beads, microbeads, microspheres, microcapsules or microparticles.

In certain embodiments of the invention, the additive material used in the invention typically has an average particle size of from 10 to 1000 µm, or 100 to 500 µm, or 125 to 250 µm or possibly, for example, 10 to 40 µm. The additive may comprise one material or may be a mixture of materials. Such additive material may act as a carrier and/or diluent for the active materials (fibrinogen and thrombin).

Additive materials that may be present in the form of particles having particle sizes of the order set out in the preceding paragraph include such additives as biocompatible water-absorbent and/or water-swellable materials, polysaccharides, porous and/or soluble materials, hollow and/or soluble materials.

In such cases, the additive material may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, by weight of the composition, or any range or value between.

Typically, the composition in such cases will comprise at least 1%, or at least 5% or at least 10% w/w of additive material, and up to 60%, up to 70% or up to 80% of additive material. Thus, the additive may be present at a level of from 1% (or 5% or 10%) to 80%, or from 1% (or 5% or 10%) to 70%, or from 1% (or 5% or 10%) to 60% w/w of the composition.

In other embodiments of the invention, the additive material typically has an average particle size of from about 10 nm to 10 µm, and may comprise one material or may be a mixture of materials.

Additive materials that may be used in the form of particles having particle sizes of the order set out in the preceding paragraph include silica, in particular hydrophilic fumed silica.

In such cases, the additive material may comprise about 0.001%, about 0.01% about 0.05%, about 0.1%, about 0.5%, about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, by weight of the composition, or any range or value between.

Typically, the composition in such cases will comprise at least 0.001%, or at least 0.01% or at least 0.05% w/w of additive material, and up to 0.1%, up to 0.5% or up to about 1 or 2% by weight of additive material. Thus, the additive may be present at a level of from 0.001% (or 0.01% or 0.05%) to 1%, or from 0.001% (or 0.01% or 0.05%) to 0.5%, or from 0.001% (or 0.01% or 0.05%) to 0.1% w/w of the composition.

In other embodiments of the invention, the additive material is not a solid, soluble material.

Various materials are suitable for use as a biocompatible, water-absorbent and/or water-swellable additive material, for enhancing flow and wettability, etc. Preferably the material is insoluble or very slowly soluble. Such materials may include dextran polymers, e.g. Sephadex, which are available in different particle sizes, starches including hetastarch, pullulan derivatives, hyaluronic acid and esters thereof, cellulose products such as microcrystalline cellulose (Avicel range), methylcellulose, carboxymethyl cellulose, microfine cellulose or hydroxy propyl cellulose, hydroxypropylmethylcellulose, hydroxypropylcellulose, low-substituted hydroxypropyl cellulose, hydroxyethylcellulose and other materials such as cross-linked polyvinyl pyrrolidone (PVP), may be used singly or in admixture. Also, suitable additive materials acting as carriers include polyethylene glycol (PEG), preferably having a molecular weight of about 1000; polyvinylpyrrolidone (PVP), preferably having an average molecular weight of about 50,000; Poly(acrylic acid), polyacrylamide, poly vinyl alcohol (PVA), Poly(methylvinylether co-maleic anhydride), Poly(ethyleneoxide), and dextran, typically having an average molecular weight of about 40,000. Microparticles of the invention may be sterilised, if necessary or desired. Sterile processing, electron beam irradiation, γ-irradiation and ethylene oxide are examples of suitable techniques.

In certain embodiments of the invention, the additive material is a silica, preferably a hydrophilic silica. Such silicas may be colloidal silicas, fumed silicas, ground silicas, precipitated silicas, or mixtures thereof. Examples of suitable fumed silicas include, but are not limited to, Aerosil® 90, 130, 150, 200, 300, 380, R202, R805, R812, R972, R974 (Degussa Corporation, Ridgefield Park, N.J.) and CAB-O-SIL® TS-720 and M-5 (Cabot Corporation, Tuscola, Ill.). Generally, Aerosil® 200, Aerosil® R974, CAB-O-SIL® TS-720 and any other generally equivalent products from other manufacturers of fumed silicas are preferred.

It is known that hydrophilic AEROSIL® colloidal silica increases the rate of tablet disintegration and active ingredient release. The colloidal silica acts as a "wick" to draw the water—for example from the digestive juices—into the interior of the tablet. Moreover, tablet ingredients "coated" with hydrophilic AEROSIL® 200 colloidal silica are more easily wetted and swell faster (disintegrants) or dissolve faster (active ingredient). Such properties enhance the wettability and dissolution of the powdered fibrin sealant of the instant invention. Furthermore, such silicas are known to act as glidants, and so will enhance the flowability, filling and delivery of such cohesive microparticulates. Moreover, such colloidal silicas are known activators for blood clotting and thus act synergistically with the fibrinogen and thrombin components (see Margolis, "The Effect of Colloidal Silica on Blood Coagulation", Aust. J. Exp. Biol., 39, pp. 249-258 (1961)).

The composition may comprise from about 0.001 to 5% w/w, about 0.01 and 2% w/w, or about 0.01 to 0.5% w/w of a silica. The silica may be simply blended with the fibrinogen-containing component and then the thrombin-containing component added thereto and blended further, or vice versa. Most preferably the silica is blended with the pre-blended first and second microparticles as a final step. Suitable blending apparatus will be known to those skilled in the art.

In a further embodiment, the silica may be present in combination with a further carrier and/or additive material, as defined herein.

In other embodiments of the invention, the additive is a highly porous and highly soluble interwoven filamentary crystal, eg of sorbitol and/or mannitol. Such materials are sold under the name PARTECK SI and PARTECK M (Merck KGaA, Darmstadt, Germany). These grades have a high adsorption capacity and so are suitable for blending with the dry powder fibrin sealant powder composition of the invention, to produce a novel powder which reduces dusting, and enhances wettability, solubilisation and performance of the dry powder fibrin sealant, by allowing blood to soak through the applied powder bed and thus avoid clotting at the powder interface alone.

The additive materials may be present in the composition of the invention as single components or in combination and may be present in the feedstock or added to either spray-dried thrombin or fibrinogen component before blending together, or added to the final blend and subjected to further blending. Such blending can be carried out using low shear or high-shear blending, mechano-chemical bonding, hybridisation or any other technique known to persons skilled in the art.

Although the components of the microparticles in a fibrin sealant of the invention are preferably water-soluble, and the microparticles are preferably obtained by spray-drying a suitable solution, the microparticles that are obtainable may be free-flowing, discrete and substantially dry or anhydrous, with a residual moisture content preferably no greater than about 8% w/w or about 5% w/w, most preferably no greater than about 3% w/w. This means that the compounds of fibrin sealant in accordance with this invention are not activated until they are wetted, e.g. by coming into contact with liquid at a wound site. The active components may therefore be delivered as a dry mixture, although separate application of the different microparticles is also envisaged. The active-containing microparticles are preferably amorphous or in the form of a glass at room temperature (e.g. 25° C.) so as to stabilise the entrapped protein as well as to present the active in such a rapidly soluble state. Preferably the active-containing microparticle composition exhibit a glass transition temperature of greater than about 25° C., or about 30° C., or about 40° C., or about 50° C. or more, as measured by Differential Scanning calorimetry or modulated Differential Scanning calorimetry. The additive material may also be amorphous or in the form of a glass at room temperature (e.g. 25° C.) so as to be in a rapidly soluble state. Preferably the additive material exhibits a glass transition temperature of greater than about 25° C., or about 30° C., or about 40° C., or about 50° C., as measured by Differential Scanning calorimetry or modulated Differential Scanning calorimetry. Such glassy compositions enable the composition to be stored at ambient or room temperature, e.g. 25° C., for extended periods of time, for example greater than 3 months or greater than 6 months, without significant losses in activity.

The additive material may also be in a crystalline or amorphous state but may also be free-flowing, discrete and substantially anhydrous, with a residual moisture content preferably no greater than 5% w/w, most preferably no greater than 3% w/w.

A dry powder fibrin sealant product may be of particular value where application to a large surface area is required. This includes surgery and repair of traumatic injuries to various organs such as the liver and spleen. A further advantageous application is in skin grafting for burns patients, and specifically where skin epidermal sheets are cultured in vitro and then transferred to the wound site. The use of fibrin sealant in the latter indication may be particularly effective in patients with extensive burns, providing a biocompatible anchorage for skin grafts. It may also be suitable in the treatment of topical ulcers.

The fibrin sealant powder composition may be applied using the powder delivery device of co-pending application PCT/GB2009/051714, herein incorporated by reference, for use in surgical interventions.

In another presentation of the powder composition, the powder is contained within a sachet or pouch of soluble material. When the pouch is placed onto moist tissue, as at a wound or surgical site, the material of the pouch dissolves to release the powder from within the pouch.

The invention will now be described, by way of illustration only, with reference to the following Examples.

Example 1

Dry powder fibrin sealant was prepared, as described in co-pending application U.S. Ser. No. 12/636,718. In brief, Fibrinogen (ZLB, Marburg, Germany) and trehalose (Pfanstiehl, Waukegan, Ill., USA) hollow spherical particles were prepared. The concentration of fibrinogen in the particles is 12% w/w.

Thrombin (SNBTS, Glasgow, Scotland) and trehalose were spray dried to obtain hollow particles.

Thrombin was present in a concentration of 1000 IU per gram of particles. The particles were blended in a 1:1 ratio; the resulting powder has a 6% w/w concentration of fibrinogen and 500 IU/gram of powder. This blend is referred to as Reference Powder.

In order to prepare the mixture of the invention, the Reference Powder was further mixed 1:1 w/w with fluid absorbing particles (Sephadex G200 superfine, GE Healthcare, Uppsala, Sweden). Sephadex G200 superfine has a dry bead size of 10-40 μm. For clarity, the resulting powder consists of 3% w/w of fibrinogen, 250 IU/gram thrombin and 50% w/w of Sephadex G200 particles. This blend is referred to as the Inventive Powder.

Efficacy Testing.

There is no universal animal model for testing efficacy of haemostat available because trauma bleeding presents itself in different forms ranging from arterial injury with high pressure to massive oozing. Large animal models (pigs) are the only models representative for the human situation (Pusateri et al. (2003) J. Trauma 55(3), 518-526). In the animal models selected, the Inventive Powder product will be compared to other products that are on the market or in development and could potentially be used in trauma applications. To simulate a traumatic injury to the liver, inducing uncontrolled severe bleeding, a liver scallop injury was inflicted on the liver of a pig by cutting away with a pair of surgical scissors a 4×5 cm wide and 1.5-2 cm deep piece from the liver (n=2). None of the veins or arteries that were cut during this procedure were tied off and the animal had received a standard dose of heparin ~15 minutes before the injury was made.

Figure 1B:
Figure 1C:

One injury was treated using the "standard" protocol in which 6 grams of Reference Powder material was poured onto the wound, covered with piece of parafilm after which pressure was applied for 30 seconds. During removal of the parafilm a substantial portion of the powder was removed as well and an additional 1.5-2 grams was applied to the wound and pressure was applied with standard surgical gauze. The bleeding slowed down significantly within 2-3 minutes, but it took ~5 minutes to obtain complete haemostasis. The second scallop injury was treated with 6 grams of Inventive Powder, having increased absorbing capacity, but only containing half of the amounts of fibrinogen and thrombin. The powder was then covered with a piece of biodegradable Vicryl sheet (Ethicon) and pressure was applied for 30 seconds using gauze. The gauze could be easily removed and the Vicryl was left on the wound to prevent disturbing the plug. No bleeding was observed and complete haemostasis was achieved within 1-1.5 minutes (see also FIG. 1). Sephadex only was not able to stop severe bleeding in animals.

This experiment clearly demonstrates the advantage of the Inventive Powder over the Reference Powder. Applying equal amounts of these powders on severe bleeding wounds results in complete hemostasis for the Inventive Powder within 1.5 minutes, whereas the Reference Powder was able to stop the bleeding in 5 minutes, but only after adding additional powder. This is surprising, as the Inventive Powder only contains half of the concentration of fibrinogen and thrombin as compared to Reference Powder. Lower concentrations of a Fibrinogen and thrombin also implies a significant reduction in the cost of Inventive Powder as compared to Reference Powder.

Example 2

In order to prepare further compositions of the invention, the Reference Powder ("FC") from Example 1 was further mixed with varying quantities of additive materials using an orbital shaker for 30 seconds or (for larger batches) a Turbula low-shear blender for 10 minutes, to produce a free-flowing powder. The following additive materials were selected, blended with the Reference Powder, and then assessed for in vitro wettability:
1. Soluble, hollow microparticles—comprising 15% w/w albumin in a glassy, spray-dried trehalose matrix ("Alb")
2. fumed silica—Aerosil 200 ("Aer")

3. polysaccharide—hetastarch (freeze-dried Voluven) ("Vol")
4. porous, soluble additive—Parteck SI 150 and 400 ("Part SI 150" and "Part SI 400")
5. porous, swellable and insoluble additive—Sephadex 200G superfine ("Sep 200G")

Figure 2:
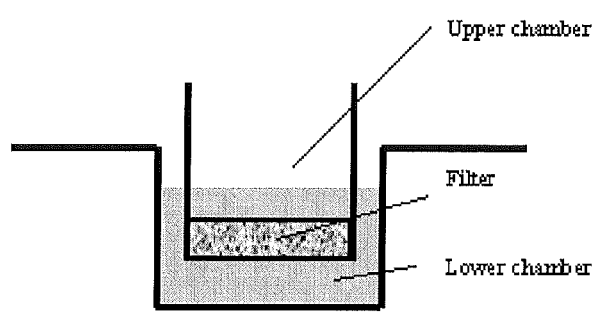
FIG. 2 is a schematic view of a modified Boyden chamber apparatus used in Example 2.
Figure 3A:
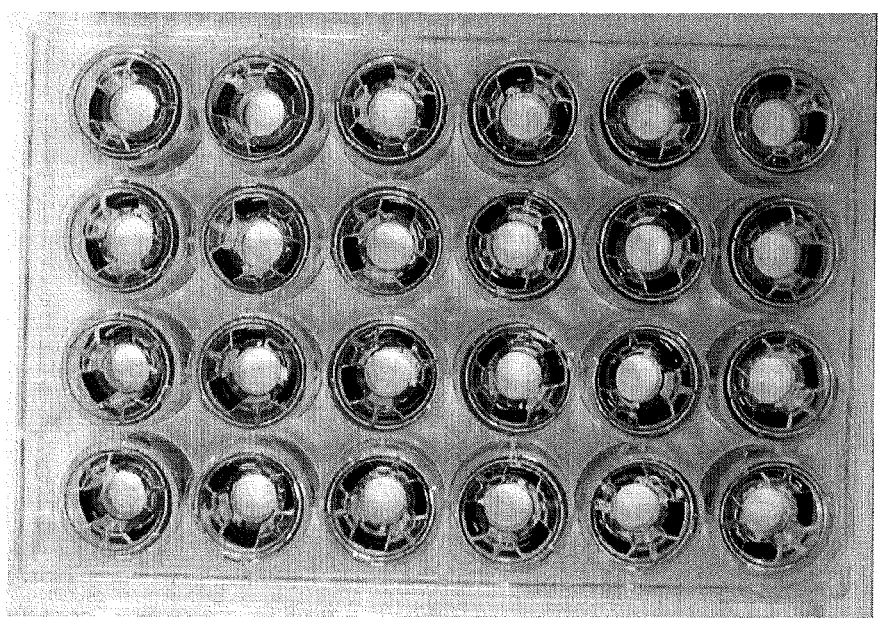
FIGS. 3a)-h) show photographs of a Boyden chamber array used in Example 2, at various time points.
Figure 3B:
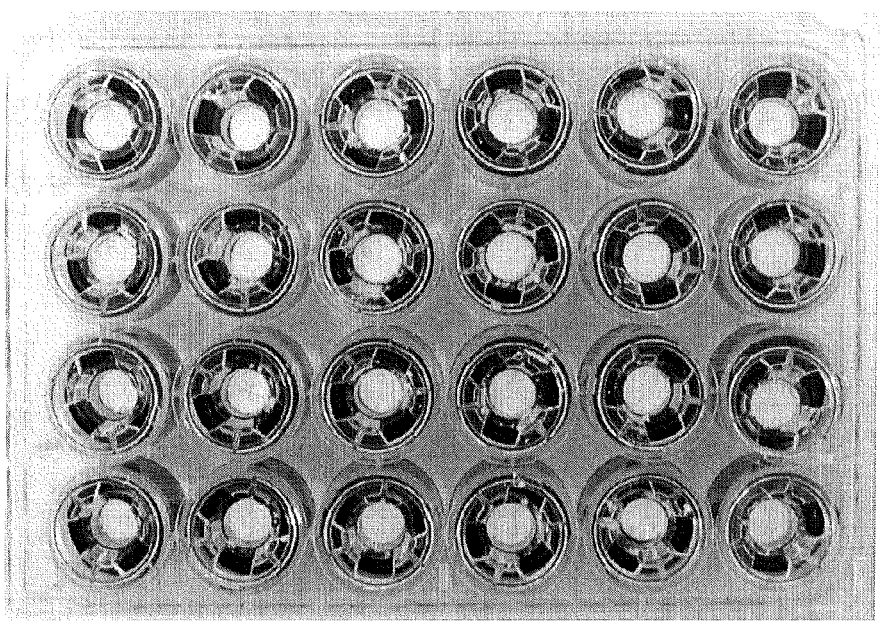
Figure 3C:
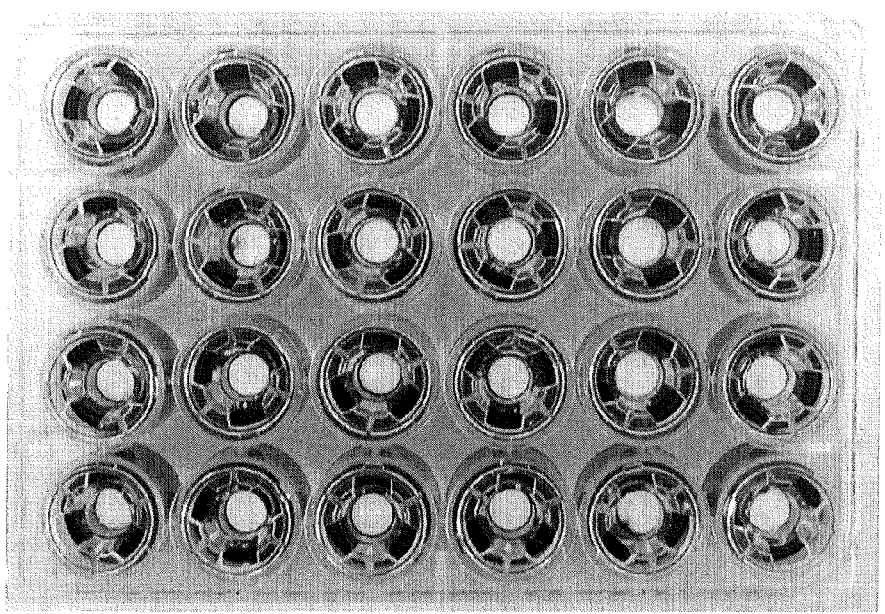
Figure 3D:
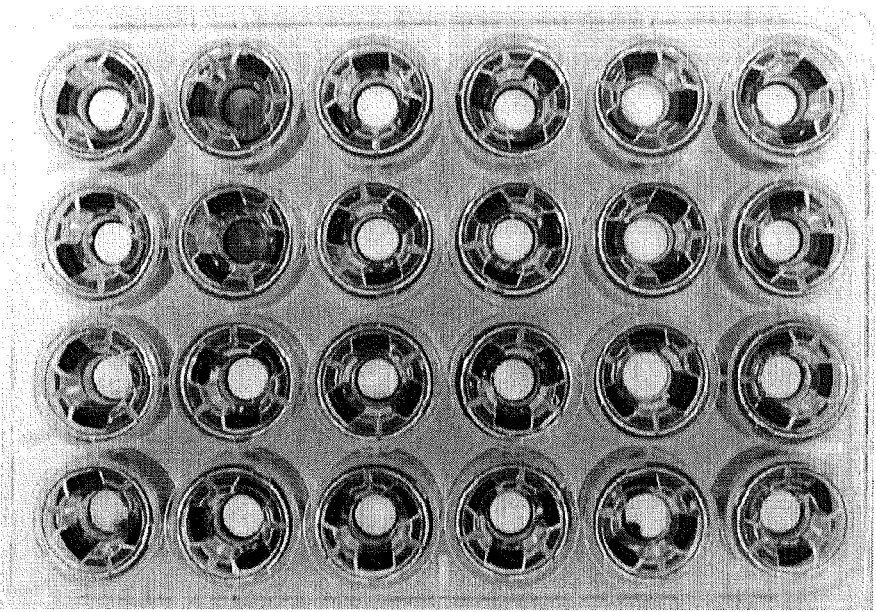
Figure 3E:
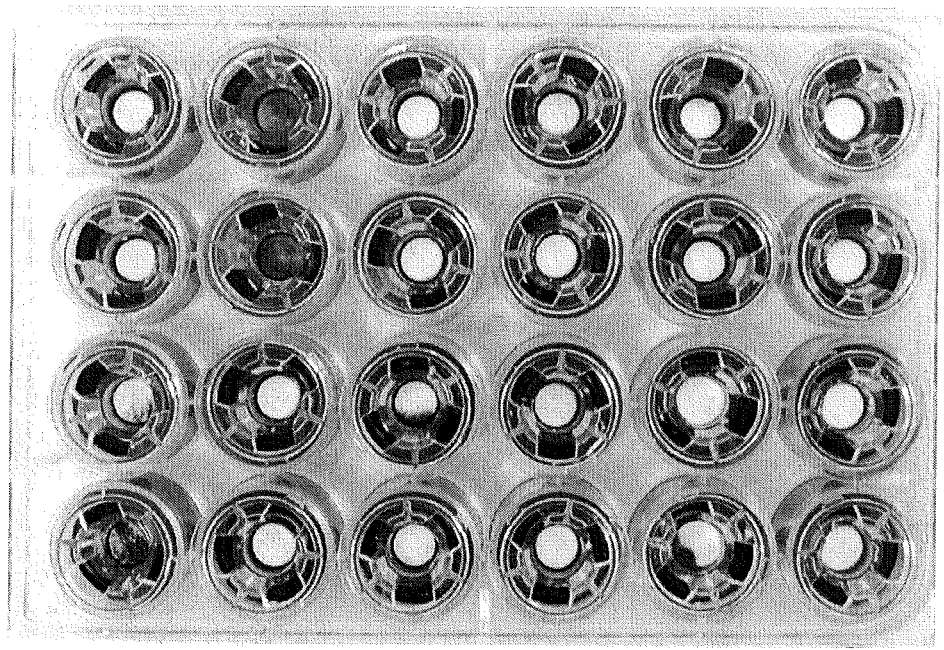
Figure 3F:
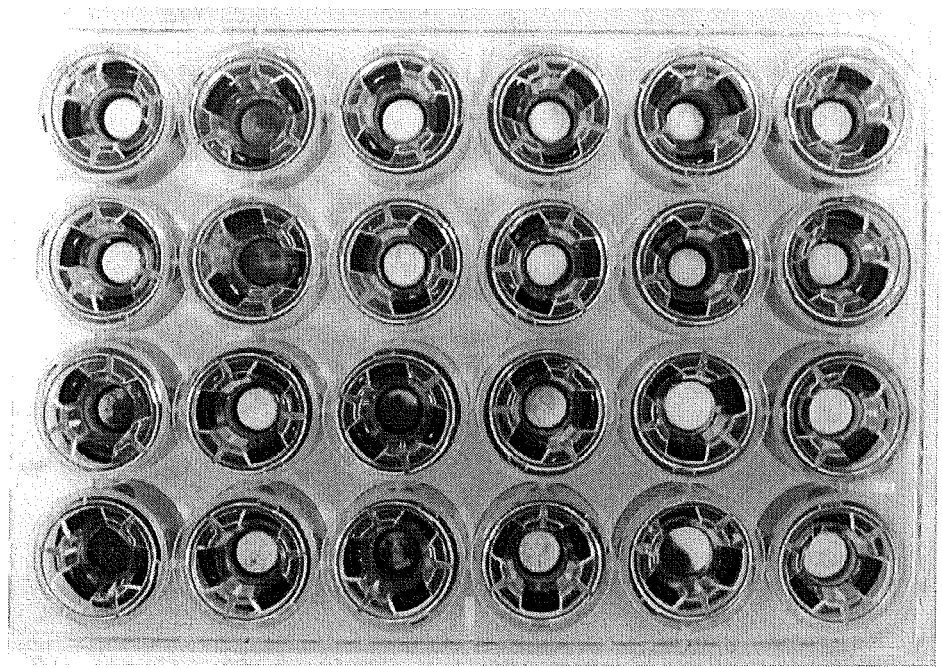
Figure 3G:
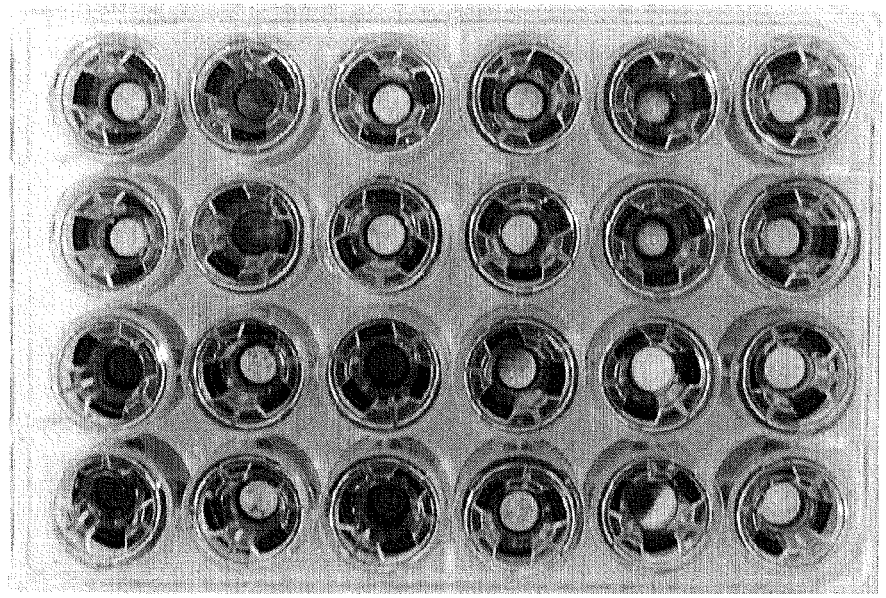
Figure 3H:
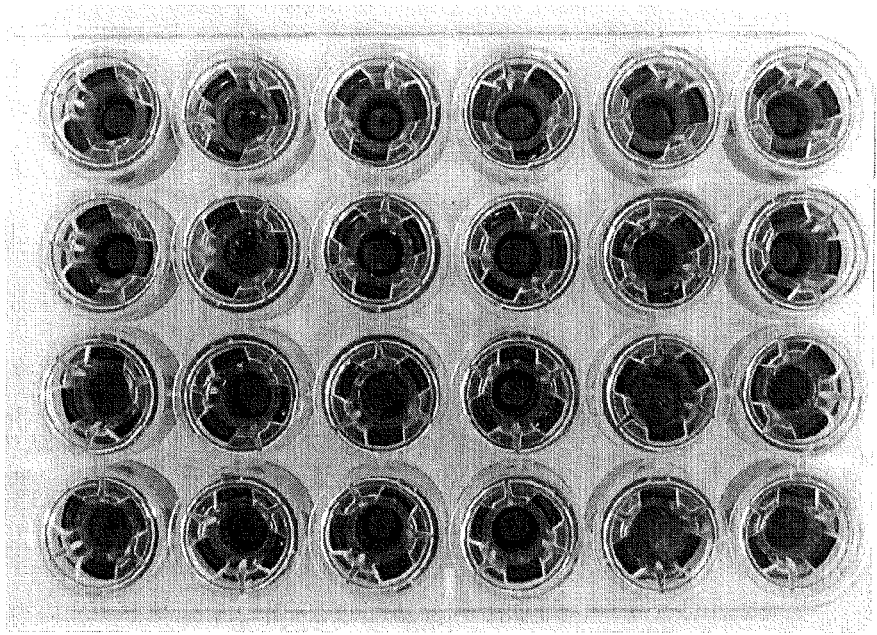

A novel in vitro wettability assay was developed using modified Boyden chambers. A Boyden chamber is essentially a chamber of two medium-filled compartments separated by a microporous membrane (see FIG. 2). In conventional use, cells are placed in the upper compartment and are allowed to migrate through the pores of the membrane into the lower compartment, where chemotactic agents are present. For the purposes of the present study (wettability analysis), the lower chamber was filled with a solution of blue dye at ambient temperature, and the test powder was filled into the upper chamber.

Twenty-four such chambers were arranged in a 4×6 array, and used to study the behaviour of the test powders, which were arranged in the manner set out in Table 1, which specifies the total weight of powder in each chamber, and the percentage of additive in each. It can be seen that Row B is a duplicate of Row A, and Row D is a duplicate of Row C.

TABLE 1

|   | 1 | 2 | 3 | 4 | 5 | 6 |
|---|---|---|---|---|---|---|
| A | 76.5 mg 0% (100% FC) | 75.0 mg 50% Alb | 77.4 mg 0.05% Aer | 74.3 mg 0.01% Aer | 75.1 mg 50% Vol | 75.8 mg 10% Vol |
| B | 75.6 mg 0% (100% FC) | 78.1 mg 50% Alb | 75.5 mg 0.05% Aer | 76.5 mg 0.01% Aer | 75.4 mg 50% Vol | 75.2 mg 10% Vol |
| C | 77.9 mg 50% Part SI 400 | 76.0 mg 10% Part SI 400 | 75.7 mg 50% Part SI 150 | 72.5 mg 10% Part SI 150 | 77.7 mg 50% Sep 200G | 76.4 mg 10% Sep 200G |
| D | 77.8 mg 50% Part SI 400 | 77.8 mg 10% Part SI 400 | 77.1 mg 50% Part SI 150 | 77.9 mg 10% Part SI 150 | 75.9 mg 50% Sep 200G | 78.0 mg 10% Sep 200G |

The powder-laden chambers were lowered into the lower chamber containing the blue dye solution and a stop-clock started. A summary of the observations is presented in Table 2:

TABLE 2

| | | | | | | |
|---|---|---|---|---|---|---|
| Time at which point blue dye appears to enter the powder from the bottom of the chamber (filter side). | 78 min | 35 min | 77 min | 74 min | 120 min | 180 min |
| | 78 min | 35 min | 77 min | 74 min | 160 min | 180 min |
| | 37 min | 55 min | 38 min | 68 min | 16 min | 68 min |
| | 37 min | 46 min | 68 min | 68 min | 16 min | 68 min |
| Time at which point the first sign of blue dye is observed at the upper surface of the powder | | 40 min | | | 223 min | |
| | | 40 min | | | 223 min | |
| | | 79 min | 174 min | 102 min | 231 min | |
| | | 68 min | 150 min | 134 min | 231 min | 17 min |
| Total surface is blue | | 93 min | | | | |
| | | 76 min | | | | |
| | | 180 min | | 180 min | | |
| | | 115 min | | 180 min | | |

Other observations noted during the analysis include:
a. For Aerosil 0.01% both of the duplicates have a big blue droplet between the powder mass and the wall of the chamber (visible T=200 side view);
b. For Parteck 10%, one of the duplicates also has a blue droplet between the powder mass and the wall of the chamber (visible T=200 side view);
c. 50% Sephadex swells up to ~5× its initial volume;
d. 10% Sephadex swells up to ~2× its initial volume;
e. Volume decrease observed at T=200 for: 50% SD Albumin
   50% Parteck SI400
   50% Parteck SI150

Photographs of the Boyden chamber array, arranged as in Table 1, at various time points are presented in FIG. 3.

As can be seen, the presence of a porous, swellable material (Sephadex), as well as hollow, soluble additive material (spray-dried albumin:trehalose), or porous, soluble large particulate additive material (Parteck SI 400), greatly enhances the water uptake of the Reference Material. Indeed, the Reference Material performed very poorly in this assay since it did not appear to absorb the blue dye solution to any great extent. The presence of very low levels of silica did not appear to greatly enhance wettability in this assay, although it may perform better in vivo, due to its interaction with the clotting process.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

The invention claimed is:

1. A method of treating a bleeding wound, comprising: administering to a bleeding wound a powder mixture comprising a homogeneous blend of:

first microparticles having an active component consisting of fibrinogen, the first microparticles having a maximum particle size, X50, between 5 μm and 50 μm;

second microparticles having an active component consisting of thrombin, the second microparticles having a maximum particle size, X50, between 5 μm and 50 μm; and an additive material selected to increase absorbance of fluid of the bleeding wound, the additive material in the form of discrete microparticles that are separate from the first microparticles and second microparticles and having an average particle size between 10 μm and 500 μm; and wherein the powder mixture comprises from 30% to 80% w/w of the additive material; and stops the bleeding in less than five minutes after contact with the bleeding wound.

2. The method according to claim 1, wherein the additive material comprises a hollow or porous material.

3. The method according to claim 1, wherein the additive material comprises a biocompatible, water-swellable material.

4. The method according to claim 1, wherein the additive material comprises a biocompatible, water absorbing material.

5. The method according to claim 1, wherein the additive material comprises a biocompatible, water-insoluble material.

6. The method according to claim 1, wherein the additive material comprises a polysaccharide.

7. The method according to claim 1, wherein the powder mixture is contained in a pouch and administered to the bleeding wound as the pouch dissolves.

8. A dry powder mixture comprising a homogeneous blend of:
- first microparticles having an active component consisting of fibrinogen, the first microparticles having a maximum particle size, X50, between 5 μm and 50 μm;
- second microparticles having an active component consisting of thrombin, the second microparticles having a maximum particle size, X50, between 5 μm and 50 μm; and
- an additive material selected to increase absorbance of fluid of the bleeding wound, the additive material in the form of discrete microparticles that are separate from the first microparticles and second microparticles and having an average particle size between 10 μm and 500 82 m; and
- wherein the powder mixture comprises from 30% to 80% w/w of the additive material; and stops the bleeding in less than five minutes after contact with a bleeding wound.

9. The powder mixture according to claim 8, wherein the additive material comprises a hollow or porous material.

10. The powder mixture according to claim 8, wherein the additive material comprises a biocompatible, water-absorbing material.

11. The powder mixture according to claim 8, wherein the additive material comprises a biocompatible, water-swellable material.

12. The powder mixture according to claim 8, wherein said first microparticles contain 0.5 to 20% w/w fibrinogen.

13. The powder mixture according to claim 8, wherein said second microparticles comprise 25 to 1000 IU/g thrombin.

14. The powder mixture according to claim 8, wherein the additive material comprises a polysaccharide.

15. A pouch comprising the powder mixture according to claim 8, wherein the pouch is configured to be applied to a wound.

16. The powder mixture according to claim 8, wherein the powder mixture has a moisture content of no greater than 5% w/w.

17. The powder mixture according to claim 8, wherein the additive material includes a dextran polymer.

18. The powder mixture according to claim 8, wherein the additive material includes soluble, hollow microparticles comprising albumin.

19. The powder mixture according to claim 8, wherein the powder mixture has a moisture content of no greater than 8% w/w.

* * * * *